United States Patent [19]

Cleare et al.

[11] 4,118,412
[45] Oct. 3, 1978

[54] PREPARATION CYANO SUBSTITUTED CYCLOPROPANE

[75] Inventors: Peter John Vernon Cleare, Ascot; Albert Edward Kaye, Greater Manchester; David John Milner, Runcorn, all of England

[73] Assignee: Imperial Chemical Industries Limited, London, England

[21] Appl. No.: 813,669

[22] Filed: Jul. 7, 1977

[30] Foreign Application Priority Data

Jul. 7, 1976 [GB] United Kingdom ............... 28240/76

[51] Int. Cl.$^2$ ........................................... C07C 121/48
[52] U.S. Cl. ..................................................... 260/464
[58] Field of Search ............................. 260/465.4, 464

[56] References Cited
U.S. PATENT DOCUMENTS

| 3,974,199 | 8/1976 | Plonka et al. ...................... 260/464 |
| 4,000,180 | 12/1976 | Punja ................................... 260/464 |
| 4,022,816 | 5/1977 | Woods et al. ...................... 260/464 |

OTHER PUBLICATIONS

Sopova, et al., J. Org. chem. U.S.S.R., 5(1969), pp. 844–849.

*Primary Examiner*—Lewis Gotts
*Assistant Examiner*—Robert C. Whittenbaugh
*Attorney, Agent, or Firm*—Cushman, Darby & Cushman

[57] ABSTRACT

A process for the preparation of cyclopropane compounds which comprises reacting a compound of formula:

$$Y-CH_2-CN$$

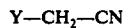

with a diene of formula:

$$CX_2=CH-CH=C(CH_3)_2$$

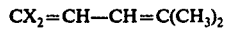

in the presence of at least one reducible copper salt, X being chlorine or bromine and Y being cyano, alkoxycarbonyl containing up to four carbon atoms in the alkoxy moiety, benzyloxycarbonyl, phenoxybenzyloxycarbonyl or 2,2-dichlorovinyloxybenzyloxycarbonyl.

18 Claims, No Drawings

PREPARATION CYANO SUBSTITUTED CYCLOPROPANE

The present invention relates to a process for the preparation of cyclopropane derivatives which are valuable chemical intermediates.

3-(2,2-Dichlorovinyl)-2,2-dimethylcyclopropane carboxylic acid is an important intermediate in the production of insecticides, including, for example, 3-phenoxybenzyl 3-(2,2-dichlorovinyl)-2,2-dimethylcyclopropane carboxylate. The preparation of 3-(2,2-dichlorovinyl)-2,2-dimethylcyclopropane carboxylic acid has been described by Farkas et al (Collection Czechoslov. Chem. Commun., (1959), 24, pp 2230–2236) by the reaction of ethyl diazoacetate with 1,1-dichloro-4-methyl-1,3-pentadiene followed by hydrolysis of the resultant ethyl ester. This process is not suitable for large scale preparation of the acid because of the difficulties of working with ethyl diazoacetate, which is a substance which can explosively decompose unless the conditions are rigorously controlled, and which is believed to be a potent carcinogen.

We have now discovered a process for the preparation of cyclopropane derivatives which avoids the use of diazoacetic esters.

Accordingly the present invention provides a process for the preparation of a compound of formula:

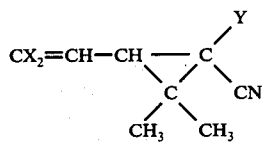
(I)

wherein X is chlorine or bromine and Y is either cyano or alkoxycarbonyl containing up to four carbon atoms in the alkoxy moiety, or benzyloxycarbonyl or substituted benzyloxycarbonyl which comprises the step of reacting a compound of formula:

$$Y—CH_2—CN \quad (II)$$

with a diene of formula:

$$CX_2=CH—CH=C(CH_3)_2 \quad (III)$$

the reaction taking place in the presence of at least one reducible copper salt.

When Y represents substituted benzyloxycarbonyl it preferebly represents phenoxybenzyloxycarbonyl or dichlorovinyloxybenzyloxycarbonyl, especially 3-phenoxybenzyloxycarbonyl or 3-(2,-dichlorovinyloxy)-benzyloxycarbonyl.

Cupric salts are preferred copper salts for use in the process and examples of cupric salts which are particularly preferred include the cupric salts of carboxylic acids, for example cupric acetate, and the salts with hydrohalic acids, for example cupric chloride. However other reducible copper salts may also be used, for example cupric sulphate.

In a preferred form the process is conducted in the presence of at least one alkali or alkaline earth metal salt, for example a lithium, calcium or magnesium salt, in addition to the reducible copper salt. Halides of lithium, calcium or magnesium are especially preferred, although other salts of these metals may also be used. Particularly useful salts of lithium, calcium and magnesium are the chlorides. Optionally a quaternary ammonium salt, for example a tetra-alkyl ammonium halide such as methyl triethyl ammonium chloride, may be used in the place of or additional to the lithium, calcium or magnesium salt.

It is also possible to conduct the process in the presence of a base which is preferably the alkali or alkaline earth metal salt of a weak acid such as carbonic acid, boric acid or a carboxylic acid (for example acetic acid). Specific examples of such bases includes potassium carbonate, borax (sodium borate), potassium acetate and calcium carbonate.

The copper, lithium and calcium salts may be used in the process of the invention in anhydrous form or they may be employed as the hydrates. Thus, for example, it is convenient to employ cupric acetate as the monohydrate and lithium chloride as the monohydrate. Calcium halides are best employed in anhydrous form.

A preferred combination of salts for use in the reaction is a mixture of cupric acetate monohydrate and lithium chloride monohydrate. Other useful combinations include cupric chloride with lithium chloride in the presence of potassium carbonate, and cupric acetate with calcium chloride.

The copper salts may be used in molar proportions with respect to the cyano derivative of formula:

$$Y—CH_2—CN$$

a preferred proportion being two moles of copper salt per mole of the cyano derivative.

Since the copper salts are reduced in the course of the reaction, it will be appreciated that it may be possible to use a suitable redox system to regenerate some or all of the reduced copper species, thus enabling the copper reagent to be used catalytically. The regeneration may be carried out in situ or in a separate stage.

The reaction may be conducted under an inert atmosphere, which may conveniently be nitrogen or argon. Alternatively, if the copper reagents are to be employed catalytically and regenerated in situ, it may be convenient to use an oxygen-containing atmosphere.

The process of the invention may optionally be carried out in the presence of a solvent or diluent for the reactants, although it may also be conducted in the absence of a solvent or diluent, the reactants themselves being nonviscous liquids although they are not necessarily good solvent for the copper and other salts employed in the process. When a solvent or diluent is used it may be for example a polar aprotic solvent or diluent of the type exemplified by dimethylformamide, dimethylsulphoxide N,N-dimethylacetamide, or an ester such as ethyl acetate or butyl acetate, or a halogenated hydrocarbon such as ethylene dichloride or methylene dichloride. Particularly preferred solvents are saturated aliphatic alcohols containing up to six carbon atoms, such as methanol, ethanol, isopropanol and t-butanol. An especially preferred solvent is ethanol, optionally denatured with small amounts of methanol as in industrial methylated spirit. Water may be used as a diluent for the reaction, particularly when a phase-transfer catalyst such as a quaternary ammonium salt is present. Examples of quaternary ammonium salts particularly useful for this purpose are tetraalkyl ammonium halides such as tetramethyl ammonium chloride, tetrabutyl ammonium chloride, ethyl trimethyl ammonium bromide, and benzyltrialkyl ammonium halides such as benzyltrimethyl ammonium chloride.

Water may also be used as a diluent in admixture with water-miscible solvents such as methanol or ethanol.

Certain combinations of solvent and copper and other salts are particularly useful in performing the invention process. These include (a) cupric acetate monohydrate, and lithium chloride monohydrate with butyl acetate, (b) cupric acetate monohydrate, and calcium chloride with ethanol, (c) cupric chloride, lithium chloride monohydrate and potassium carbonate with butyl acetate, and (d) cupric acetate with methyltriethyl ammonium chloride in butyl acetate.

It will be appreciated that the cyclopropane derivatives of formula I (where Y is not cyano) can exist in cis and trans isomeric forms. The proportion of each form present in the product appears to be dependent to some extent on the choice of solvent or diluent and the salt or salts used. Thus a particularly useful combination for yielding a product with an excess of cis - isomer present is cupric acetate and calcium chloride with ethanol.

The process may be conducted at any temperature within the range 0° C. to the reflux temperature of the reactants and solvent or diluent (when used). However it has been found that the reactions are accelerated by the application of heat and a preferred temperature range for conducting the process is from about 50° C. to about 105° C.

The process may be conducted over a time period of from several minutes to several hours, for example from 30 minutes to 30 hours. A time of about 5 hours is normally sufficient to provide a reasonable yield of product when a temperature in excess of 75° C. is employed.

The direct products of the process are compounds of Formula I as defined hereinabove. Of particular interest are compounds of Formula I wherein X is chlorine, and Y is lower alkoxycarbonyl, for example the following:
methyl 1-cyano-3-(2,2-dichlorovinyl)-2,2-dimethyl-cyclopropane carboxylate, and
ethyl 1-cyano-3-(2,2-dichlorovinyl)-2,2-dimethyl cyclopropane carboxylate.

Preferred compounds of Formula II for use in the process of the invention are lower alkyl esters of cyanoacetic acid, for example methyl cyanoacetate and ethylcyanoacetate.

If the process is conducted with a lower alkyl ester of cyanoacetic acid in the presence of a polar aprotic solvent or diluent such as dimethylformamide or dimethylacetamide, and the reaction mixture is maintained at a temperature in excess of 120° C. for a period in excess of about 24 hours there may be formed in addition to the compound of Formula I, an amount of the compound derived by decarbalkoxylation of the compound of Formula I, for example the compound 1-cyano-3-(2,2-dichlorovinyl)-2,2-dimethylcyclopropane.

The compounds of Formula I obtained by the invention process may be readily converted by hydrolysis and decarboxylation to the corresponding carboxylic acids.

The invention is illustrated by the following Examples, wherein all parts are by weight.

EXAMPLE 1

151 Parts of 1,1-dichloro-4-methylpenta-1,3-diene, 226 parts of ethyl cyanoacetate, 200 parts of cupric acetate monohydrate, 148 parts of cupric chloride, 62.6 parts of lithium chloride monohydrate and 1884 parts of dimethylformamide are stirred under an atmosphere of nitrogen. The temperature is raised to 100° C. and maintained at 100°–105° C. for 40 minutes. After cooling, the low-boiling components of the mixture are removed by heating to 80° C. at a pressure of 12 mm Hg to leave 806.6 parts of residue. The residue, 1740 parts of toluene, 2360 parts of hydrochloric acid (s.g. 1.18) and 3000 parts of water are stirred at ambient temperature for 30 minutes. The organic layer is separated and extracted twice with 590 parts of hydrochloric acid (s.g. 1.18) in 500 parts of water and finally four times with 500 parts of water. The toluene solution is evaporated by heating to 85° C. at a pressure of 17 mm Hg to yield 183.2 parts of ethyl 1-cyano-3-(2,2-dichlorovinyl)-2,2-dimethylcyclopropane-1-carboxylate (yield 49.1% based on a strength of 69.9%).

EXAMPLE 2

A similar reaction but omitting the dimethylformamide yielded 248.4 parts of ethyl 1-cyano-3-(2,2-dichlorovinyl)-2,2-dimethylcyclopropane-1-carboxylate (estimated strength 63.5% equivalent to 60.6% yield).

EXAMPLE 3

151 Parts of 1,1-dichloro-4-methylpenta-1,3-diene, 113 parts of ethyl cyanoacetate, 200 parts of cupric acetate monohydrate, 148 parts of cupric chloride, 62.6 parts of lithium chloride monohydrate and 900 parts of ethyl acetate are stirred in an atmosphere of nitrogen. The temperature is raised to 80° C. and maintained at 80°–81° C. for 5 hours. After cooling, the reaction mixture was stirred with 1180 parts of hydrochloric acid (s.g. 1.18) and 1500 parts of water for 10 minutes. The organic layer was separated and extracted twice with 590 parts of hydrochloric acid (s.g. 1.18) in 500 parts of water. The ethyl acetate solution was diluted with 900 parts of ethyl acetate and the solution washed four times with 500 parts of water. The ethyl acetate solution is evaporated by heating to 87° C. at 20 mm Hg pressure to yield 201 parts of ethyl 1-cyano-3-(2,2-dichlorovinyl)-2,2-dimethylcyclopropane-1-carboxylate (estimated strength 82.7% equivalent to 63.4% yield).

EXAMPLE 4

A similar reaction to Example 2 but reducing the ethyl cyanoacetate charge to 113 parts gave 232 parts of ethyl 1-cyano-3-(2,2-dichlorovinyl)-2,2-dimethylcyclopropane-1-carboxylate of lower strength (estimated strenght 57.6% equivalent to 51.0% yield).

EXAMPLE 5

A similar reaction to Example 2 but reacting at 20°–25° C. for 26 hours gave 201 parts of ethyl 1-cyano-3-(2,2-dichlorovinyl)-2,2-dimethylcyclopropane-1-carboxylate of low strength (estimated strength 20.5%).

EXAMPLE 6

A mixture of 1,1-dichloro-4-methyl-1,3-pentadiene (7.55g), ethyl cyanoacetate (11.3g), anhydrous cupric sulphate (15.96g), lithium chloride monohydrate (3.13g) and dimethylformamide (50 ml) was heated with stirring under a nitrogen atmosphere at 99° to 106° C. for 5 hours and 20 minutes. After cooling to the ambient temperature the insoluble material was removed by filtration. The filtrate was heated under reduced pressure and the more volatile portion boiling at up to 106° C./13 mm.Hg distilled off. The residue was partitioned between toluene (50 ml) and a water (75 ml) and concentrated (s.g. 1.18) hydrochloric acid (50 ml) mixture.

The organic layer was separated, washed twice with a water (50 ml) and concentrated hydrochloric acid (50 ml) mixture, and then four times with water (25 ml). After removal of the more volatile portion boiling up to 111° C./21 mm. Hg, the residual oil (3.187 g) was analysed by gas liquid chromatography and shown to contain 76% of ethyl 1-cyano-3-(2,2-dichlorovinyl)-2,2-dimethylcyclopropane carboxylate.

EXAMPLE 7

The procedure of Example 3 was followed except that an equivalent amount of benzyl cyanoacetate was used in place of ethylcyanoacetate. The product was benzyl 1-cyano-3-(2,2-dichlorovinyl)-2,2-dimethylcyclopropane carboxylate.

EXAMPLE 8

The procedure of Example 3 was repeated except that an equivalent amount of 3-phenoxybenzyl cyanoacetate was employed. The crude product contained 71% of 3-phenoxybenzyl 1-cyano-3-(2,2-dichlorovinyl)-2,2-dimethylcyclopropane carboxylate, equivalent to a yield of 77.7%.

EXAMPLE 9

The procedure of Example 3 was repeated except that ethanol was used as a diluent in place of ethyl acetate. The crude product contained 75.6% of ethyl 1-cyano -3-(2,2-dichlorovinyl)-2,2-dimethylcyclopropane carboxylate equivalent to a yield of 62.6%.

EXAMPLE 10

The procedure of Example 9 was followed in a series of experiments except that in each case a different diluent was used. Satisfactory yields of product were obtained when the diluent was selected from the following list:

80% aqueous acetonitrile
t-butanol
diethylene glycol dimethyl ether (diglyme)
tetrahydrofuran
dimethyl sulphoxide
acetonitrile
cyclohexanol
isopropanol
dimethoxyethane
N-methyl-2-pyrrolidone
methanol
dimethylformamide
methyl chloride
ethylene dichloride
chlorobenzene
toluene Lower yields (18 to 25%) were obtained when water, glacial acetic acid or tetrachloroethylene were used as diluents.

EXAMPLE 11

The procedure of Example 3 was followed except that butyl acetate was used in place of ethyl acetate. A satisfactory yield of product was obtained when the lithium chloride was replaced by a molar equivalent of methyl triethyl ammonium chloride.

EXAMPLE 12

The procedure of Example 9 was followed in a series of experiments except that in each case the molar equivalent of lithium chloride was replaced by one of:

(a) a 0.1 molar equivalent of lithium chloride
(b) a molar equivalent of calcium chloride
(c) a molar equivalent of magnesium chloride
(d) a molar equivalent of potassium chloride.

Satisfactory yields of product were obtained in each experiment. In a similar experiment where the lithium chloride was simply omitted, a slightly lower yield resulted.

EXAMPLE 13

The procedure of Example 1 was followed except that a molar equivalent of cupric chloride was used in place of the cupric acetate (that is two molar equivalents of of cupric chloride in all) and a molar equivalent of potassium acetate or potassium carbonate or borax was present. In each case a satisfactory yield was obtained.

We claim:

1. A process for the preparation of a compound of formula:

$$CX_2=CH-CH\underset{\underset{CH_3}{\diagdown}\underset{CH_3}{\diagup}C}{\overset{\diagup Y}{\underset{\diagdown CN}{\diagdown C\diagup}}}$$

wherein X is chlorine or bromine and Y is cyano, alkoxycarbonyl containing up to four carbon atoms in the alkoxy moiety, benzyloxycarbonyl, phenoxybenzyloxycarbonyl or 2,2-dichlorovinyloxybenzyloxycarbonyl, which comprises the step of reacting a compound of formula:

$$Y-CH_2-CN$$

with a diene of formula:

$$CX_2=CH-CH=C(CH_3)_2$$

in the presence of at least one reducible copper salt.

2. The process as claimed in claim 1 in which the reducible copper salt is a cupric salt.

3. The process as claimed in claim 2 in which the cupric salt is cupric acetate or cupric chloride.

4. The process as claimed in claim 3 conducted in the presence of at least one member of the group consisting of lithium chloride or calcium chloride.

5. The process as claimed in claim 3 carried out in the presence of methyltriethyl ammonium chloride.

6. The process as claimed in claim 3 carried out in the presence of a base selected from the group consisting of potassium carbonate, sodium borate, potassium acetate and calcium carbonate.

7. The process as claimed in claim 2 in which the reducible copper salt is cupric acetate monohydrate and there is also present lithium chloride monohydrate.

8. The process as claimed in claim 2 which the reducible copper salt is cupric chloride and there is also present lithium chloride and potassium carbonate.

9. The process as claimed in claim 1 in which the reducible copper salt is cupric acetate and there is also present calcium chloride.

10. The process as claimed in claim 1 wherein there are present two molar equivalents of copper salt per molar equivalent of the compound of formula:

$$Y-CH_2-CN$$

and the reaction is carried out in the presence of a diluent for the reactants selected from the group consisting of an ester, a saturated aliphatic alcohol containing up to six carbon atoms and water.

11. The process as claimed in claim 10 in which the diluent is butyl acetate or ethyl acetate.

12. The process as claimed in claim 10 in which the diluent is methanol, ethanol, isopropanol or t-butanol.

13. The process as claimed in claim 10 in which the diluent is water, and the process is conducted in the presence of a phase-transfer catalyst which is a tetraalkyl ammonium halide or a benzyl trialkyl ammonium halide.

14. The process as claimed in claim 10 in which the reducible copper salt is cupric acetate monohydrate, and there is also present lithium chloride monohydrate, and the diluent is butyl acetate.

15. The process as claimed in claim 10 in which the reducible copper salt is cupric acetate monohydrate, and there is also present calcium chloride, and the diluent is ethanol.

16. The process as claimed in claim 10 in which the reducible copper salt is cupric acetate, and there is also present methyl triethyl ammonium chloride, and the diluent is butyl acetate.

17. The process as claimed in claim 10 in which the reducible copper salt is cupric chloride, and there is also present lithium chloride monohydrate and potassium carbonate, and the solvent or diluent is butyl acetate.

18. The process as claimed in claim 17 conducted at a temperature within the range 50° C. to 105° C.

* * * * *